United States Patent
Shwe et al.

(10) Patent No.: US 6,250,138 B1
(45) Date of Patent: Jun. 26, 2001

(54) DETERMINING FLUID BUBBLE POINT PRESSURE USING AN ADJUSTABLE CHOKE

(75) Inventors: Than Shwe; Mike Flecker; Steve Thompson; Roy Torrance, all of Houston, TX (US)

(73) Assignee: Wood Group Logging Services Holdings, Inc., Houston, TX (US)

( * ) Notice: Subject to any disclaimer, the term of this patent is extended or adjusted under 35 U.S.C. 154(b) by 0 days.

(21) Appl. No.: 09/241,890

(22) Filed: Feb. 1, 1999

(51) Int. Cl.[7] ............................. G01N 13/00; E21B 47/12
(52) U.S. Cl. ...................... 73/64.54; 166/264; 73/152.02
(58) Field of Search ................................ 73/61.46, 64.54, 73/64.46, 865.6, 152.02, 152.16, 152.24, 152.26, 152.51, 152.55; 166/264, 270.1, 401

(56) References Cited

U.S. PATENT DOCUMENTS

| | | |
|---|---|---|
| 4,782,695 * | 11/1988 | Glotin et al. ...................... 73/152.51 |
| 4,860,581 * | 8/1989 | Zimmerman et al. ............. 73/152.26 |
| 5,579,842 | 12/1996 | Riley . |
| 5,635,631 | 6/1997 | Yesudas et al. . |
| 5,706,892 | 1/1998 | Aeschbacher, Jr. et al. . |
| 6,058,773 * | 5/2000 | Zimmerman et al. ............. 73/152.24 |

* cited by examiner

Primary Examiner—Hezron Williams
Assistant Examiner—Jay L. Politzer
(74) Attorney, Agent, or Firm—Haynes & Boone L.L.P.; Todd Mattingly

(57) ABSTRACT

A method of determining the real time bubble point pressure of a fluid originating from a subsurface earth formation using an adjustable choke positioned downhole adjacent to the formation. The adjustable choke is placed into communication with the wellbore fluid flowing from the formation to the surface. The adjustable choke has a remotely adjustable choke opening for selectively restricting the flowrate of the fluid flowing through the choke. The adjustable choke has a pressure sensor for measuring the fluid pressure downstream of the choke opening. The method includes obtaining downstream fluid pressure data as a function of choke size for generating a plot of downstream pressure versus choke size data which exhibits substantially linear behavior having two different slopes. Extrapolating a best-fit line through the set of data having a first slope so as to intersect an extrapolation of a best-fit line through the set of data having a second slope thereby provides the bubble point pressure of the fluid as the pressure corresponding to the intersection of the two lines.

10 Claims, 3 Drawing Sheets

DETERMINING FLUID BUBBLE POINT PRESSURE USING AN ADJUSTABLE CHOKE

Background of the Invention

This invention relates generally to the field of wireline tools used for subsurface earth formation testing, and more particularly to wireline tools used for determining the bubble point pressure of fluid flowing from a subsurface formation.

Electric wireline tools are used for determining bubble point pressure of fluid originating from a subsurface earth formation in order to determine properties of the fluid used in calculating the total fluid content within the formation. One of the methods of determining in situ bubble point pressure of formation fluid involve the use of downhole electric wireline tools capable of withdrawing a sample of fluid from a subsurface earth formation into a sample chamber and incrementally expanding the volume of the sample chamber while measuring the pressure. The bubble point pressure of the fluid is then extracted from a plot of the pressure versus volume data. These conventional tools are used only in the exploration stage, are not useable during well production, and are removed from the wellbore prior to flowing the well.

Other conventional methods of determining bubble point pressure of a formation fluid involve withdrawing a sample of fluid from the earth formation into a chamber of a testing tool. Then, the bubble point pressure measurement is done at the well site or laboratory by measuring the pressure and volume of the sample, while expanding the volume of the sample. Such conventional tools are not permanently installed, and do not permit the determination of in situ fluid bubble point pressure during well production.

Conventional methods and apparatus for remotely controlling well production employ the use of various downhole electromechanical devices coupled with computer based surface systems. One such device is an adjustable choke with pressure sensors located upstream and downstream of the choke for attaining desired wellbore pressure by controlling fluid flow during the life of the well. However, such devices do not use the adjustable choke in determining a bubble point pressure of the fluid.

Therefore, a need exists for a method for determining fluid bubble point pressure during well production.

The present invention is directed to overcoming one or more of the limitations of the existing devices.

Summary of the Invention

According to one aspect of the present invention, an apparatus for determining a bubble point pressure of a fluid originating from a subsurface earth formation is provided that includes production tubing, an adjustable choke, and a controller. The production tubing is adapted for placement within the subsurface earth formation. The adjustable choke is coupled to the production tubing. The adjustable choke includes a remotely adjustable choke opening adapted to selectively restrict a flow rate of a fluid flowing through the choke opening, and a pressure sensor adapted to measure a fluid pressure downstream of the choke opening. The controller is operably coupled to the adjustable choke and is adapted to control the adjustable choke opening, monitor the fluid pressure downstream of the choke opening, and calculate the bubble point pressure.

According to another aspect of the present invention, a method of determining a bubble point pressure of a fluid originating from a subsurface earth formation is provided that includes placing an adjustable choke in communication with the fluid flowing from the subsurface formation. The size of the adjustable choke is selectively adjusted to vary the flow rate downstream from the adjustable choke. The fluid pressure downstream from the adjustable choke is measured for a range of choke sizes. The plot of the fluid pressure downstream against choke size will indicate fluid phase change from one phase (liquid), as shown by a first line, into two phases (liquid and gas), as shown by a second line. The intersection of these two best fit lines indicates the bubble point pressure for the fluid.

According to another aspect of the present invention, a method of determining a bubble point pressure of a fluid originating from a subsurface earth formation using an adjustable choke positioned downhole adjacent to the formation is provided that includes placing the adjustable choke in communication with the fluid flowing from the formation to the surface during well production. The adjustable choke has a selectively operable actuator for remotely adjusting the size of an opening of the choke in order to vary the downstream flowrate of the fluid flowing through the opening. The choke also includes a pressure sensor located adjacent to the choke opening for measuring the downstream pressure of the fluid after flowing through the choke opening. The pressure sensor communicates the pressure measurements to a controller. The size of the adjustable choke is selectively adjusted to varying the downstream fluid flowrate while simultaneously measuring the downstream fluid pressure. Downstream fluid pressure data at several choke sizes is obtained to generate a first plot of downstream pressure vs choke size data which contains data exhibiting substantially linear behavior having a first slope and a second plot of downstream pressure vs choke size data which contains data exhibiting substantially linear behavior having a second slope. The plotted data are then extrapolated to determine the intersection of the first and second plots to determine the bubble point pressure of the fluid.

Detailed Description of the Illustrative Embodiments

Figure 1:
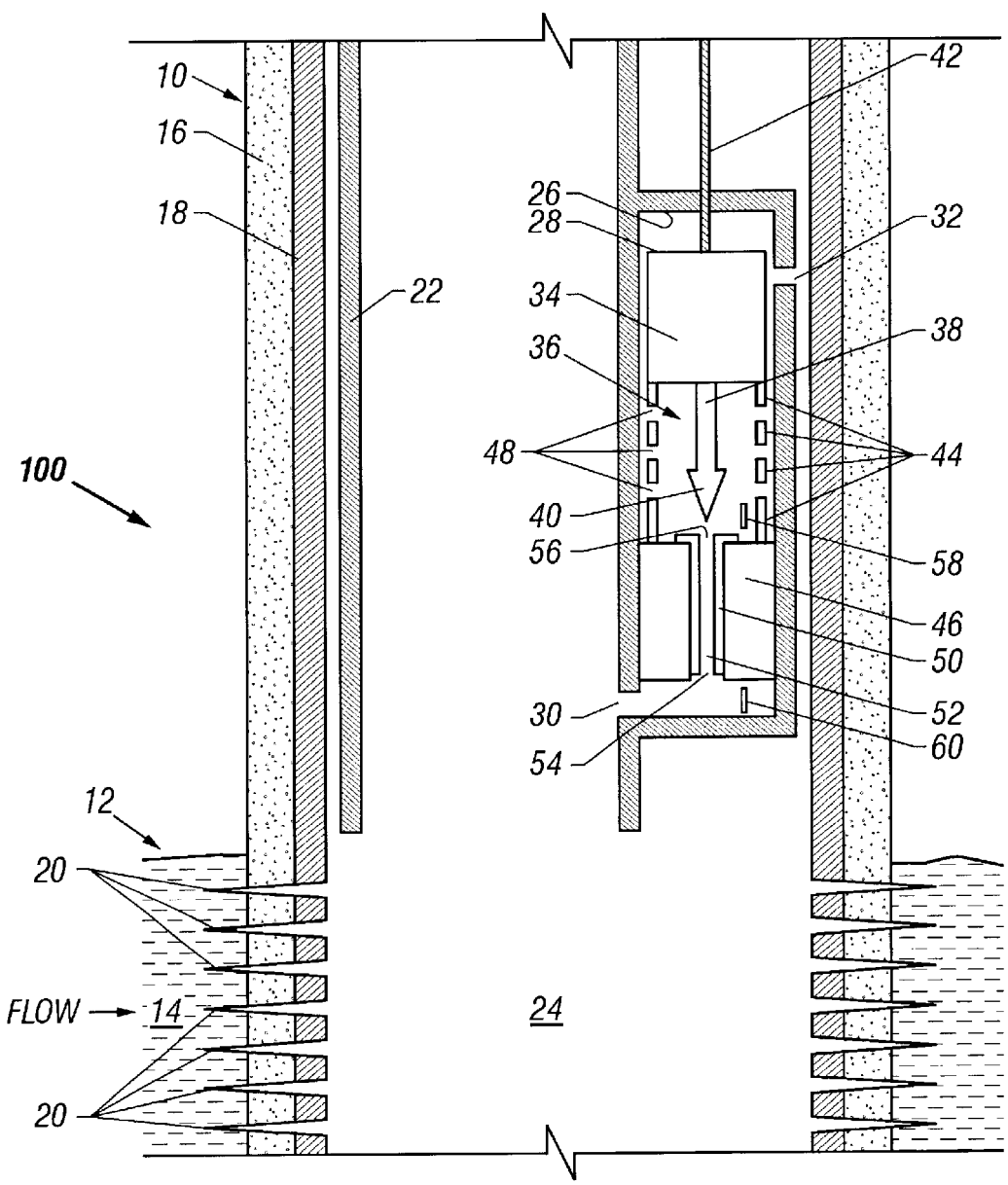
FIG. 1 depicts a view, partly in cross-section, of an embodiment of an adjustable choke positioned inside an inverted pocket of a production tubing with pressure transducers positioned above and below an opening of the choke for measuring the downstream and upstream pressures, respectively, of fluid flowing through the fully open choke.

Referring initially to FIG. 1, a preferred embodiment of an apparatus 100 for determining bubble point pressure positioned in a wellbore 10 is illustrated. The wellbore 10 includes a hole drilled through the earth penetrating a subsurface earth formation 12 containing formation fluid 14. The wellbore 10 is lined with annular regions of cement 16 and a casing 18. Perforations 20 adjacent to the formation 12 provide a passage permitting formation fluid 14 to flow from the formation 12 into a lower end of production tubing 22. The production tubing 22 provides a conduit for facilitating the flow of wellbore fluid 24, originating from the formation 12, to the surface.

The apparatus 100 includes an adjustable choke 28 disposed within an inverted pocket 26 of the tubing 22. The adjustable choke 28 controllably restricts the flow of wellbore fluid 24 in the pocket 26 and thereby induces a loss in the fluid flowrate and pressure across the choke 28. Wellbore fluid 24 flows from the tubing 22 into an inlet port 30 of the pocket 26, through the adjustable choke 28, and out of the pocket 26 through an outlet port 32.

The adjustable choke 28 includes a motor 34 for vertically translating a bidirectional conical needle 36 which extends from a bottom side of the motor 34. The bidirectional conical needle 36 incorporates a vertical linear spindle 38 and a right circular cone 40 wherein the cone 40 opens upward and has an axis of symmetry coincident with the longitudinal axis of the spindle 38. The spindle 38 connects on an upper end to the bottom side of the motor 34, and on a lower end the spindle 38 connects to a top side of the cone 40.

The motor 34 is powered by an armored electrical cable or wireline 42 attached to a top side of the motor 34. In addition, the motor 34 is supported by a cylindrical support member 44 which connects on an upper end to the bottom side of the motor 34, and on a lower end connects to a top side of an annular mounting block 46. The support member 44 is perforated with holes 48 to enable the fluid to flow out of the choke 28 toward the upper end of the pocket 26. An outer diameter surface of the annular mounting block 46 attaches along an inner surface of the pocket 26. A needle seating 50 attaches along the top side of the annular mounting block 46 and extends downwardly along an inner diameter surface of the annular mounting block 46.

The needle seating 50 includes a constant diameter passage 52 having an inlet opening 54 at the passage 52 on a lower end of the needle seating 50 and an outlet opening 56 at the passage 52 on an upper end of the needle seating 50. A pressure transducer 58 located in an immediate area above the outlet opening 56 measures a downstream pressure of the wellbore fluid 24 after flowing through the outlet opening 56 of the adjustable choke 28.

Another pressure transducer 60 located in an immediate area below the inlet opening 54 measures the fluid pressure upstream of the adjustable choke 28.

Figure 2:
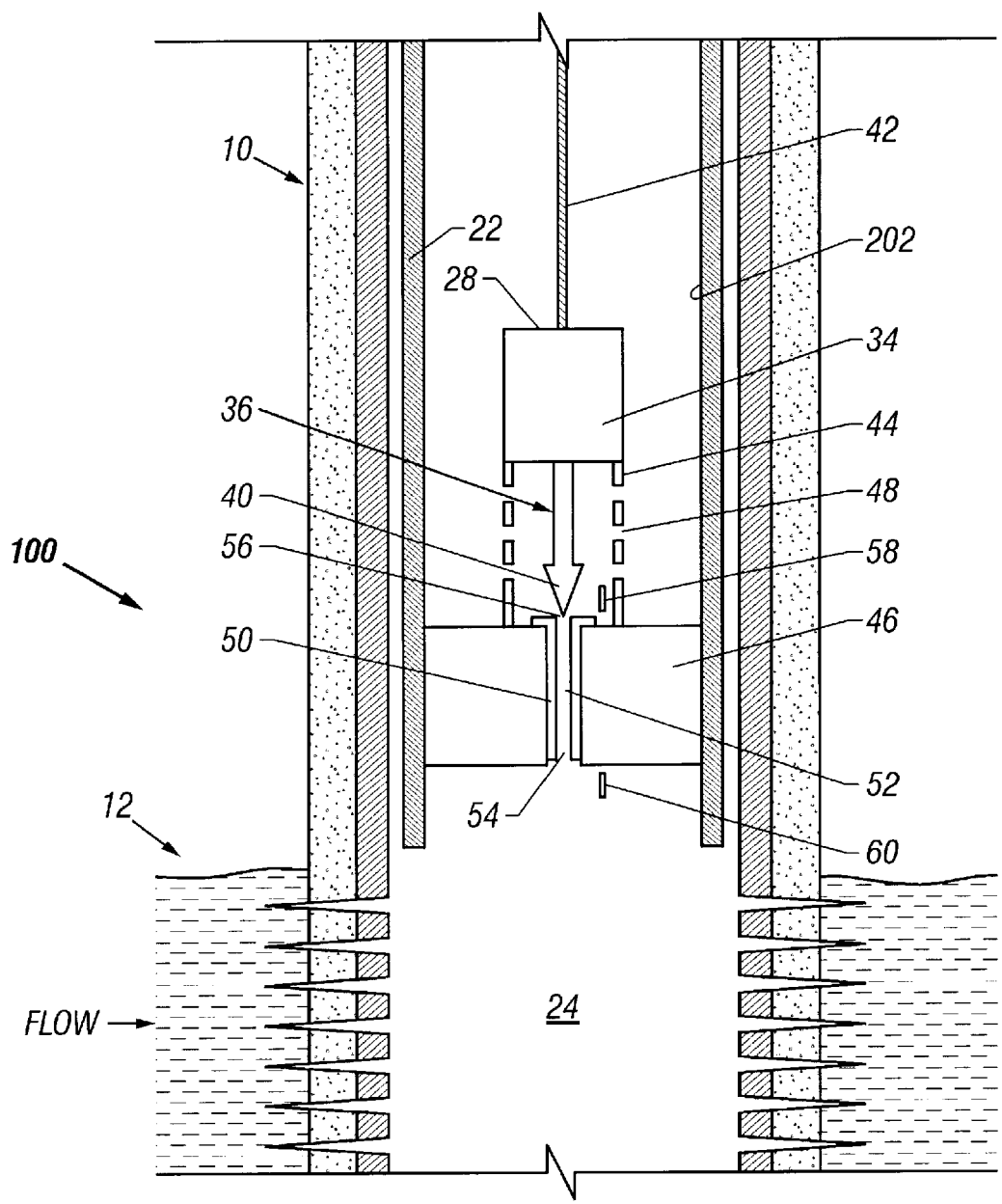
FIG. 2 depicts a view, partly in cross-section, of an alternate embodiment in which an adjustable choke is positioned inside a primary bore of a production tubing, illustrating a means of adjusting the choke size by physically displacing area available for the passage of fluid.

Referring to FIG. 2, an alternate embodiment 200 in which the adjustable choke 28 is disposed within a primary bore 202 of the tubing 22 is illustrated. In this embodiment, an annular mounting block 46 is sized so that an outer diameter surface of the annular mounting block 46 attaches along an inner surface of the primary bore 202. The adjustable choke 28 controllably restricts the flow of wellbore fluid 24 in the tubing 22 and thereby induces a loss in the fluid flowrate and pressure across the choke 28.

In a preferred embodiment, the adjustable choke 28 including elements 34, 36, 38, 40, 42, 44, 46, 48, 50, 52, 54, 56, 58 and 60 comprises the adjustable choke included in the commercially available product entitled "The Cobra System" manufactured and sold by DataLine Petroleum Services in Houston, Tex. modified in accordance with the teachings of the present disclosure.

In operation, the adjustable choke 28 is placed into communication with the wellbore fluid 24, as illustrated in both FIGS. 1 and 2. A controller (not illustrated) remotely adjusts the choke size of the adjustable choke 28 by sending electrical control signals through the wireline 42 to the motor 34 for controlling the penetration depth of the bidirectional conical needle 36 into a plane of the outlet opening 56. Extending a vertex of the conical needle 36 so as to penetrate the outlet opening 56 physically displaces an area in the plane of the outlet opening 56 by the presence of a circular cross-sectional area of the cone 40. In a preferred embodiment, the plane of the outlet opening 56 is perpendicular to the axis of the cone 40. Increasing the penetration depth of the cone 40 into the outlet opening 56, increases the cross-sectional area of the cone 40 in the plane of the outlet opening 56 and thereby decreases the choke size or effective open area of the outlet opening 56 available for the passage of wellbore fluid 24. Generally, the smaller the choke size, the smaller the flowrate of wellbore fluid 24 through the outlet opening 56 and, consequently, the smaller the corresponding downstream pressure, as pressure is proportional to flowrate. The pressure transducer 58 located downstream of the outlet opening 56 is used to measure the downstream fluid pressure for several different choke sizes ranging from completely open to nearly completely closed. When the choke size is adjusted such that the corresponding downstream pressure is equal to or less than a bubble point pressure of the wellbore fluid 24, gas releases from solution and separates from the liquid phase thereby forming a two-phase mixture of liquid and gas.

Figure 3:
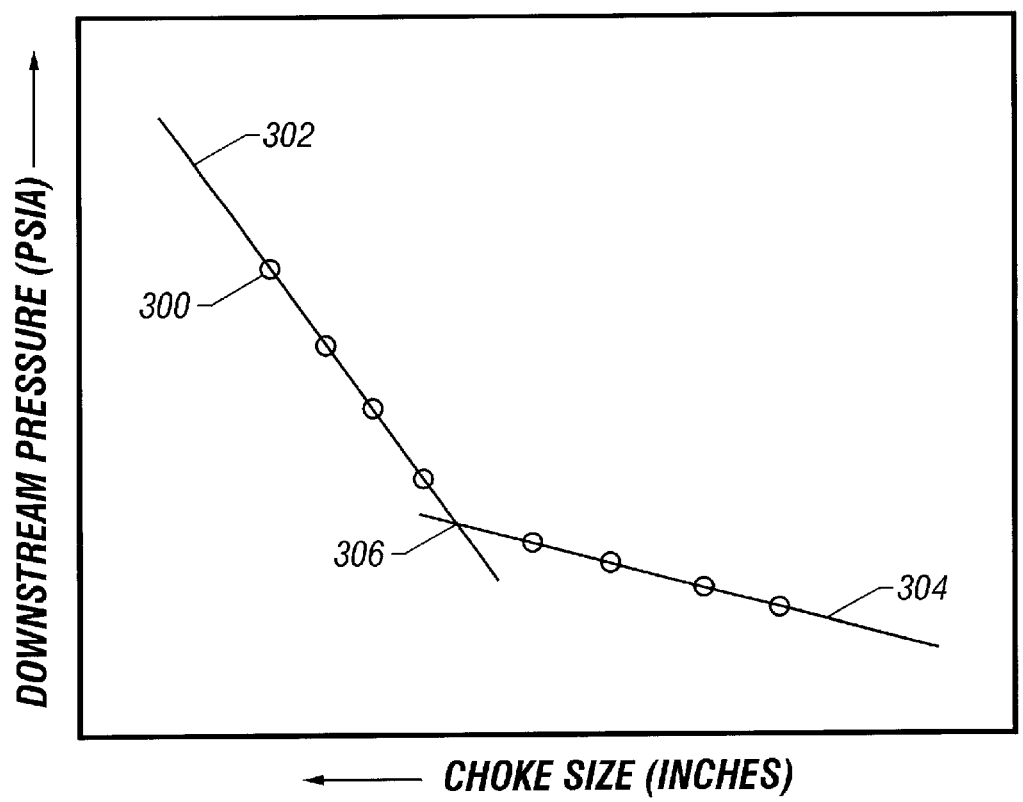
FIG. 3 illustrates the use of downstream pressure vs choke size for determining a bubble point pressure of a fluid.

Referring to FIG. 3, a method for determining the bubble point pressure of the wellbore fluid from the monitored downstream pressure will be described. In FIG. 3 a plot of downstream pressure versus choke size data 300 exhibiting two different linear slopes is illustrated. The downstream pressure is monitored using the pressure transducer 58. A first best-fit line 302 drawn through the substantially linear data exhibits a first slope. A second best-fit line 304 drawn through the substantially linear data exhibits a second slope. The first best-fit line 302 corresponds to pressures at which the wellbore fluid is a single phase liquid wherein gas remains in solution. The second best-fit line 304 corresponds to pressures at which gas releases from solution and the wellbore fluid is a two-phase gas-liquid mixture. The bubble point pressure 306 of the wellbore fluid is the pressure that corresponds to the intersection of the two extrapolated best-fit lines 302 and 304. In a preferred embodiment, the determination of the bubble point pressure 306 is performed by the controller using conventional curve-fitting software.

Referring back to FIG. 2, the adjustable choke 28 may also be used for conducting a downhole build up pressure transient test while minimizing wellbore storage effects. Upon shut in of the wellbore 10, the pressure transducer 60 located in an immediate area below the inlet opening 54 measures the fluid pressure upstream of the adjustable choke 28 as the pressure builds up. Anomalies in the pressure data due to wellbore storage effects are minimized by positioning the adjustable choke 28 downhole so as to minimize the volume or length of the wellbore 10 between the location of shutting in the wellbore 10 and the formation 12.

A method of determining a bubble point pressure of a production fluid using an adjustable choke positioned downhole adjacent to a subsurface earth formation has been described. The adjustable choke is placed in communication with the fluid flowing from the formation to the surface in order to vary the pressure of the fluid flowing through the choke. Adjusting the choke size by selectively restricting the area of the choke available for the passage of fluid induces losses in the fluid flowrate and pressure across the choke. A pressure transducer in an immediate area downstream of the choke provides a means of measuring the pressure of the fluid as a function of choke size. A plot of downstream pressure versus choke size data exhibits substantially linear behavior having a first slope corresponding to pressures at which the fluid is a single phase liquid and a second, smaller slope corresponding to pressures at which the fluid is a two-phase liquid-gas mixture. Extrapolating a best-fit line drawn through the single phase fluid data so as to intersect an extrapolation of a best-fit line drawn through the two phase fluid data thereby determines the bubble point pressure of the fluid as the pressure corresponding to the intersection of the two lines.

Although illustrative embodiments of the invention have been shown and described, a wide range of modification, changes and substitution is contemplated in the foregoing disclosure. In some instances, some features of the present invention may be employed without a corresponding use of the other features. Accordingly, it is appropriate that the appended claims be construed broadly and in a manner consistent with the scope of the invention.

What is claimed is:

1. An apparatus for determining a bubble point pressure of a fluid originating from a subsurface earth formation, comprising:
 a production tubing adapted for placement within the subsurface earth formation; an adjustable choke coupled to the production tubing, the adjustable choke including:
  a remotely adjustable choke opening for selectively restricting a flow rate of a fluid flowing through the choke opening; and
  a pressure sensor for measuring a fluid pressure downstream of the choke opening; and
 a controller operably coupled to the adjustable choke for controlling the adjustable choke opening, monitoring the fluid pressure downstream of the choke opening, and calculating the bubble point pressure during the flowing of fluid from the subsurface formation through the production tubing by:
  generating a first plot of downstream pressure vs. choke size which exhibits substantially linear behavior having a first slope and a second plot of downstream pressure vs. choke size which exhibits substantially linear behavior having a second slope; and
  determining the intersection of the first plot and the second plot.

2. The apparatus of claim 1, wherein the production tubing includes an inner fluid passage and an outer surface, and wherein the adjustable choke is in fluidic communication with the inner fluid passage.

3. The apparatus of claim 2, wherein the adjustable choke is positioned on the outer surface of the production tubing.

4. The apparatus of claim 2, wherein the adjustable choke is positioned within the inner fluid passage of the production tubing.

5. A method of determining a bubble point pressure of a fluid originating from a subsurface earth formation, comprising:
 placing an adjustable choke in communication with the fluid flowing from the subsurface formation;
 selectively adjusting the size of the adjustable choke to vary the flow rate downstream from the adjustable choke;
 measuring the fluid pressure downstream from the adjustable choke and the corresponding choke size for a range of choke sizes;
 generating a first plot of downstream pressure vs. choke size which exhibits substantially linear behavior having a first slope and a second plot of downstream pressure vs. choke size which exhibits substantially linear behavior having a second slope; and
 determining the intersection of the first plot and the second plot.

6. The method according to claim 5, wherein the adjustable choke is positioned downhole within an inverted pocket of a production tubing, the tubing having a primary bore and a pocket which is laterally separated from the primary bore by an inner wall, the pocket having an inlet port at a lower end of the pocket for the entrance of fluid flowing from inside the primary bore and an outlet port at an upper end of the pocket for the fluid to exit the pocket.

7. The method according to claim 5, wherein the adjustable choke is positioned downhole within a primary bore of a production tubing.

8. The method according to claim 6, wherein a longitudinal axis of the pocket is substantially parallel to a longitudinal axis of the tubing.

9. A method of determining a bubble point pressure of a fluid originating from a subsurface earth formation using an adjustable choke positioned downhole adjacent to the formation, comprising:
 placing the adjustable choke in communication with the fluid flowing from the formation to the surface during well production, the choke having a selectively operable actuator for remotely adjusting the size of an opening of the choke in order to vary the downstream flowrate of the fluid flowing through the opening, the choke including a pressure sensor located adjacent to the choke opening for measuring the downstream pressure of the fluid after flowing through the choke opening, the pressure sensor communicating the pressure measurements to a controller;
 selectively adjusting the choke size for varying the downstream fluid flowrate and simultaneously measuring the downstream fluid pressure;
 obtaining downstream fluid pressure data at several choke sizes for generating a plot of downstream pressure vs choke size data which contains data exhibiting substantially linear behavior having a first slope and data exhibiting substantially linear behavior having a second slope; and
 extrapolating the data demonstrating a first slope by a best-fit line so as to intersect an extrapolation of the data demonstrating a second slope, thereby determining the bubble point pressure of the fluid as the pressure corresponding to the intersection of the two lines.

10. An apparatus for determining a bubble point pressure of a fluid originating from a subsurface earth formation, comprising:
 means for placing an adjustable choke in communication with the fluid flowing from the subsurface formation;
 means for selectively adjusting the size of the adjustable choke to vary the flow rate downstream from the adjustable choke;
 means for measuring the fluid pressure downstream from the adjustable choke and the corresponding choke size for a range of choke sizes;
 means for generating a first plot of downstream pressure vs. choke size which exhibits substantially linear behavior having a first slope and a second plot of downstream pressure vs. choke size which exhibits substantially linear behavior having a second slope; and
 means for determining the intersection of the first plot and the second plot.

* * * * *